United States Patent [19]

Potter

[11] Patent Number: 5,111,821
[45] Date of Patent: May 12, 1992

[54] FLUOROMETRIC METHOD FOR DETECTING ABNORMAL TISSUE USING DUAL LONG-WAVELENGTH EXCITATION

[75] Inventor: William R. Potter, Grand Island, N.Y.

[73] Assignee: Health Research, Inc., Buffalo, N.Y.

[21] Appl. No.: 268,723

[22] Filed: Nov. 8, 1988

[51] Int. Cl.⁵ ............................................. A61B 5/00
[52] U.S. Cl. ..................................... 128/654; 128/665
[58] Field of Search ............................ 128/633–634, 128/664, 665, 666, 654

[56] References Cited

U.S. PATENT DOCUMENTS

| | | | |
|---|---|---|---|
| 4,449,535 | 5/1984 | Renault | 128/665 |
| 4,541,438 | 9/1985 | Parker et al. | 128/664 |
| 4,556,057 | 12/1985 | Hiruma et al. | 128/634 |
| 4,576,178 | 3/1986 | Johnson | 128/670 |
| 4,718,417 | 1/1988 | Kittrell | 128/634 |
| 4,889,129 | 12/1989 | Dougherty et al. | |
| 4,930,516 | 6/1990 | Alfano et al. | |

OTHER PUBLICATIONS

Pottier, R. H. et al., Photochemistry and Photobiology (1986) 44(5):679–687.

Primary Examiner—Ruth S. Smith
Attorney, Agent, or Firm—Morrison & Foerster

[57] ABSTRACT

A method and apparatus for in vivo detection of abnormal tissue in patients by irradiating a diagnostic region simultaneously with at least two wavelengths of incident light, and detecting the resulting fluorescence of normal and abnormal tissue. The patient is provided with a photosensitizer which preferentially collects in abnormal tissue, and beams of light—preferably at about 612 and 632.8 nm—are directed to the diagnostic region. The beams of light are chopped at 90 and 135 Hz, respectively. Fluorescent light from the diagnostic region is then detected, and an electronic signal is generated relating to the intensity of the fluorescence. Because of the chopping of the incident beams, the fluorescent light and the resulting electronic signal are also chopped. The electronic signal is provided as input to phase-locked amplifier circuitry, which differentiates between the contribution to the signal resulting from each of the 612 and 632.8 nm incident beams. A difference signal is provided as output to headphones, and the operator of the apparatus is notified of presence of abnormal tissue by changes in pitch of the difference signal. The source for the light may be lasers or an arc lamp, and there may be three or more incident wavelengths used.

7 Claims, 14 Drawing Sheets

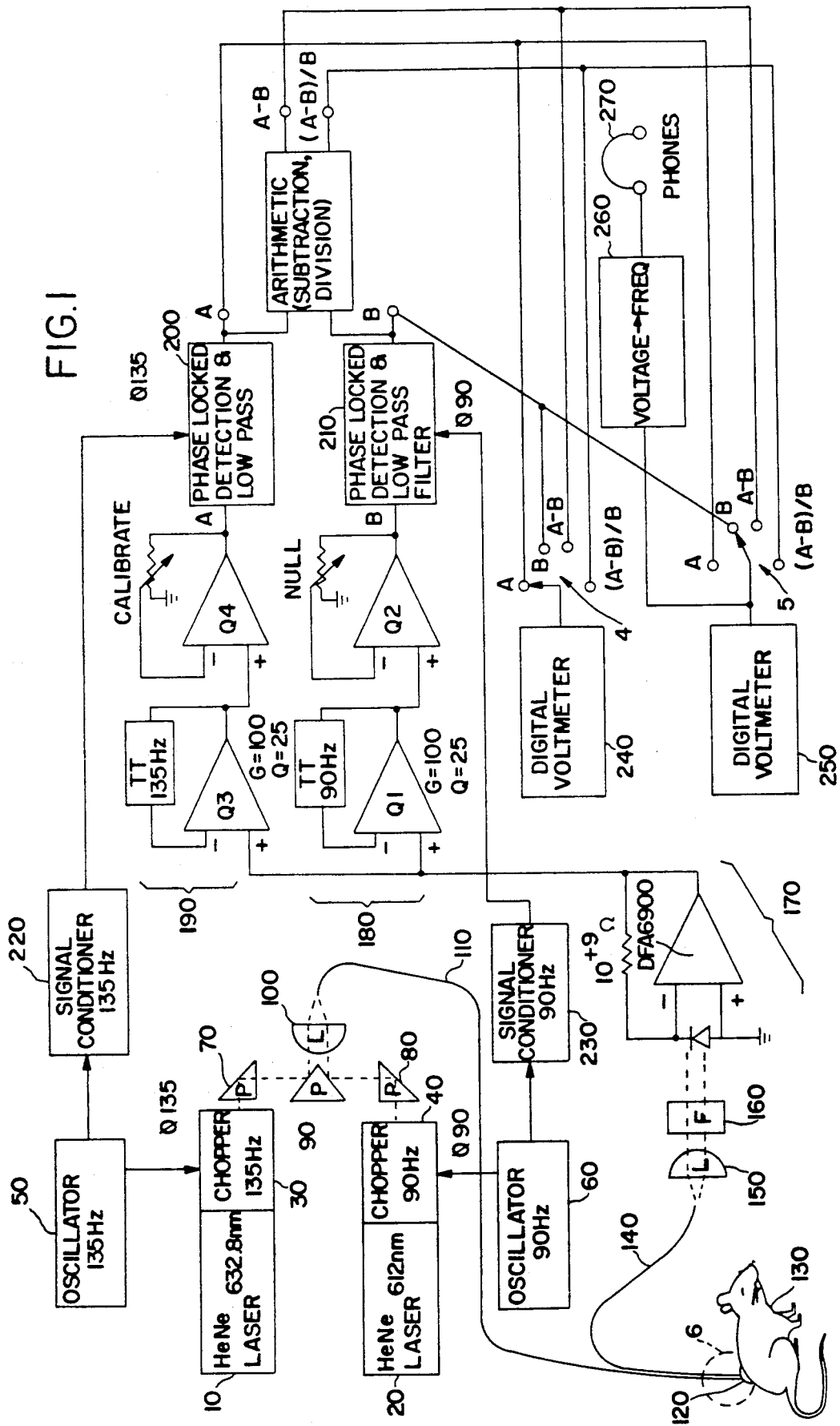

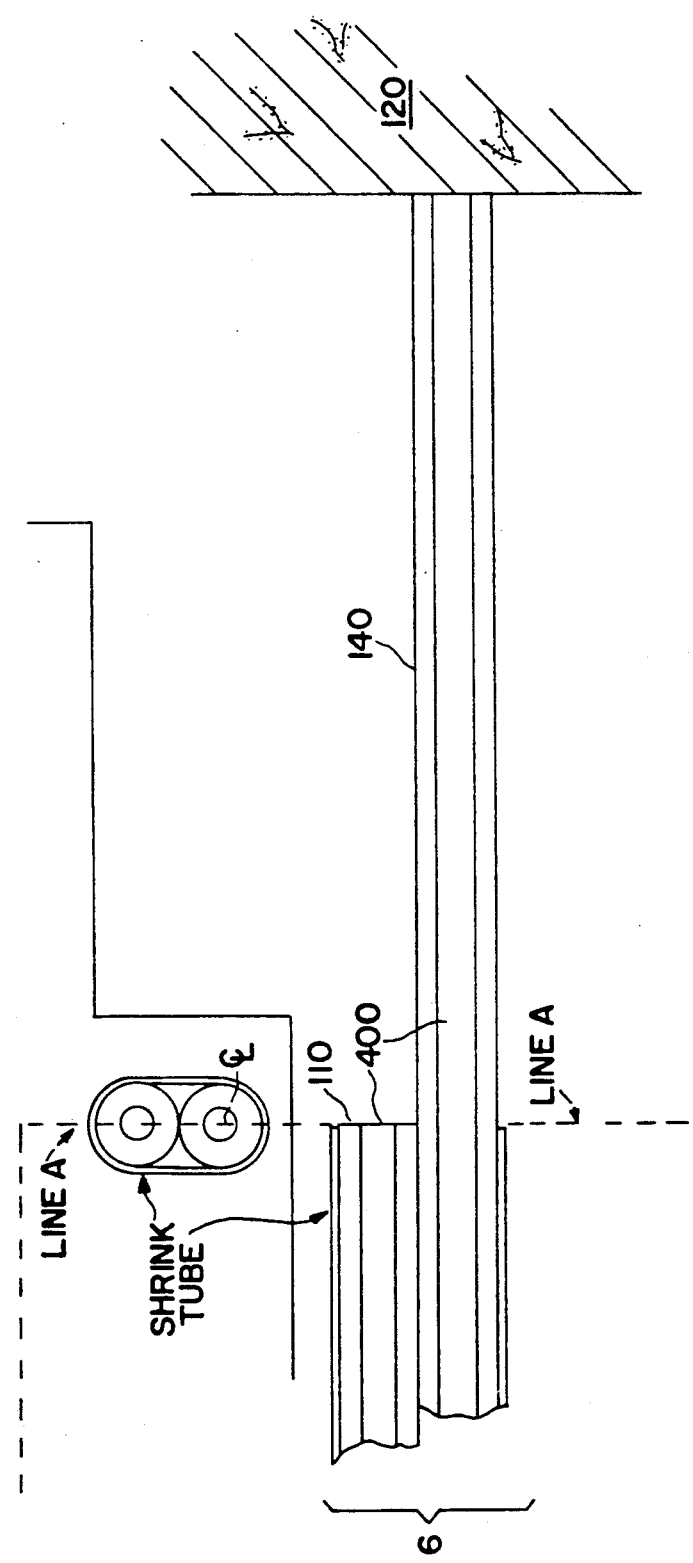

FLUOROMETRIC METHOD FOR DETECTING ABNORMAL TISSUE USING DUAL LONG-WAVELENGTH EXCITATION

BACKGROUND OF THE INVENTION

Animal tissues contain traces of materials, such as protoporphyrin, which fluoresce at a wavelength of 690 nm when excited by visible light. Such fluorescence is described, for example, in the article by R. H. Pottier et al., "Non-Invasive Technique for Obtaining Fluorescence Excitation and Emission Spectra In Vivo," *Photochemistry and Photobiology*, Vol. 44 pp. 679-687 (1986). Tissue fluorescence is also discussed in the article by William R. Potter and Thomas S. Mang, "Photofrin II Levels By In Vivo Photometry," *Progress in Clinical and Biological Research*, Vol. 170 pp. 177-186 (1984). The above articles are incorporated herein by reference.

The fluorescent tumor localizing photosensitizer Photofrin II is retained by abnormal tissue such as tumors at a higher level than most surrounding normal tissues, and therefore it is diagnostically useful to supply Photofrin II to the tissues, and then to illuminate the tissue with light to detect by the fluorescent response whether abnormal tissue is present.

In the therapeutic use of this material (referred to as photodynamic therapy, or PDT), large doses of 630 nm light are used both to activate the fluorescence of the sensitizer (such as Photofrin II) and to selectively destroy the tumor by a photochemical reaction However, the fluorescent response of tissues may be created by excitation using incident light with wavelengths in the 600 nm region, which is in the visible spectrum, and thus there is a problem with stray light causing fluorescence which may be interpreted as arising from abnormal tissue. Thus, there is a need for a system which can accurately differentiate between fluorescence arising from sensitizer in normal tissue and that arising from sensitizer in abnormal tissue, especially in vivo. In addition, there is a need for distinguishing between fluorescence arising from low levels of fluorescent tumor localizers (i.e., sensitizers such as Photofrin II) and natural tissue background fluorescence.

There is especially a need for a fluorometer which can detect abnormal cells which are within a mass of tissue, such as within a group of lymph nodes, without the need for slicing the tissue open and inspecting each sliced segment in a superficial manner, as has been done in the past. Thus, it is an object of this invention to provide a method and apparatus of fluorometry with the capability of effectively penetrating a mass of tissue for purposes of detecting abnormal tissue.

One characteristic of presently used PDT methods is the need to use therapeutic levels of the sensitizer which result in highly photosensitive skin for long periods of time, often on the order of four to six weeks. This skin sensitivity requires the patient to remain indoors during daylight hours after injection until the photosensitivity has decreased.

Thus, long and high photosensitivity is a significant disadvantage to the use of this drug for detection or localization. The need to use high levels of the drug is a result of the natural background fluorescence of the tissue, which tends to vary in a random fashion from point to point.

In one system, an imaging device uses 400 nm absorption for superficial excitation of bladder tissue. H. Baumgartner et al., "A Fluorescent Imaging Device for Endoscopic Detection of Early Stage Cancer—Instrumental and Experimental Studies," *Photochemistry and Photobiology*, Vol. 46, No. 5, pp. 759-763 (1987). In this system, tissue is first scanned using light in the violet region of the spectrum, and a subsequent scan with green or blue light from an argon laser is used to excite the tissue background and subtract this contribution to the image. There are certain disadvantages to this approach, however, one of which is that the tissue excitation by the two wavelengths is done in an alternating fashion, such that real-time images of in vivo tissues are not achievable, since registration of the image would have to be maintained for the two excitation wavelengths. Furthermore, it would be impractical to use this type of imaging with light in the 600 nm range because scattering of the light by tissue would cause resolution to be very poor.

However, imaging with wavelengths of light in the 600 nm range is highly desirable because of the deep penetration of such wavelengths. There is therefore a need for a system for in vivo fluorometry which produces real-time images which may utilize longer wavelengths for noninvasive examination of tissue to the maximum depth possible, especially for use with handheld probes. There is also a need for a system which utilizes relatively low levels of sensitizing chemicals such as Photofrin II, so as to greatly reduce or eliminate clinically significant photosensitivity.

It is an object of this invention to provide a method and apparatus for in vivo fluorometry which can be implemented in a handheld nonimaging probe where sequential tissue excitation is not feasible.

SUMMARY OF THE INVENTION

The present invention comprises a method and apparatus, including an in vivo fluorometer, employing simultaneous dual long-wavelength excitation to cancel tissue background fluorescence by subtraction. The apparatus of the invention includes two lasers for providing two beams of incident light, one at 612 nm and one at 632.8 nm. The light beams are chopped, i.e. periodically interrupted, by a tuning fork chopper, one at 90 Hz and the other at 135 Hz, at two other chopping frequencies chosen to exclude mutual harmonics. The two beams are combined into one diagnostic beam by means of prisms and a lens, and are directed through an optical fiber to a diagnostic region of a patient or animal pretreated with Photofrin II or some other local tumor photosensitizer.

Both normal and abnormal tissue will fluoresce as a result of the incident beams, and a receive fiber is coupled to the transmission fiber to pick up such fluorescence. The transmission and receive fibers are coupled together in a fixed geometrical relationship, forming a probe.

The fluorescent signal is filtered by a 690 (~10) nm optical interference filter, and is converted to an electronic signal with a signal strength related to the intensity of the fluorescence The electronic signal is provided as input to each of two tuned amplifier circuits, which are designed to filter out the contributions to the fluorescent signal from the two incident beams. Thus, one filter effectively extracts the contribution to the fluorescence which results from the 612 nm beam, and the other extracts the contribution resulting from the 632.8 nm beam. An A channel and a B channel are provided in the circuitry for carrying the two electronic signals.

The apparatus is calibrated in advance to ensure that, when no abnormal tissue is present, the A channel signal equals the B channel signal. If abnormal tissue is present in the patient, the A channel signal will increase significantly, due to the fluorescence of the sensitizer in the abnormal tissue. A signal (A-B) is generated by subtraction circuitry, and is converted to an audio signal with an audio frequency related to the magnitude of the difference, and the audio signal is provided as an output to headphones for the operator of the apparatus. The operator is thus notified of the presence of abnormal tissue by an increase in the frequency of the audio signal.

Circuitry may also be provided to generate a signal (A-B)/B, which is independent of the distance from the probe to the diagnostic region, and is also independent of other factors which influence the fluorescent signal such as attenuation due to a tumor being situated beneath a layer of other tissue. The operator may optionally select the (A-B)/B signal for input to the headphones, and digital voltmeters are also provided for visual display of the A, B, A-B and (A-B)/B signals.

An oscillator circuit is provided for driving the choppers and for providing a phase-lock signal to each of the A and B channels for accurate detection of the respective contributions to fluorescence from the two incident wavelengths. The phase-lock signal is conditioned by removing harmonics and converting it to a sine-wave signal.

Thus, the apparatus and method of the invention accomplish the needs described above, including providing real-time in vivo detection of abnormal tissue and avoiding erroneously identifying normal tissue as abnormal. Low levels of photosensitizers such as Photofrin II may be used without loss of accuracy of the results, and natural tissue background fluorescence is precisely subtracted out of the fluorescent signal. Use of wavelengths in the 610 and 630 nm range both allows for deep penetration of the tissue and takes advantage of an intensity peak for Photofrin II.

BRIEF DESCRIPTION OF THE DRAWINGS

FIG. 1 is a block diagram showing a dual excitation wavelength fluorometer of the invention.

FIG. 10 is a sectional view of a node probe of the invention.

DESCRIPTION OF THE PREFERRED EMBODIMENTS

As shown in FIG. 1, the apparatus of the invention includes two lasers such as HeNe lasers 10 and 20, in front of which are placed choppers 30 and 40. The choppers may be model L40 HHD tuning fork choppers with a Type HEA-5A2 driver, produced by American Time Products division of Frequency Control Products, Inc. of Woodside, N.Y. The integrated circuits shown in FIG. 1 are available from Analog Devices of Norwood, Mass.

Figure 1A:
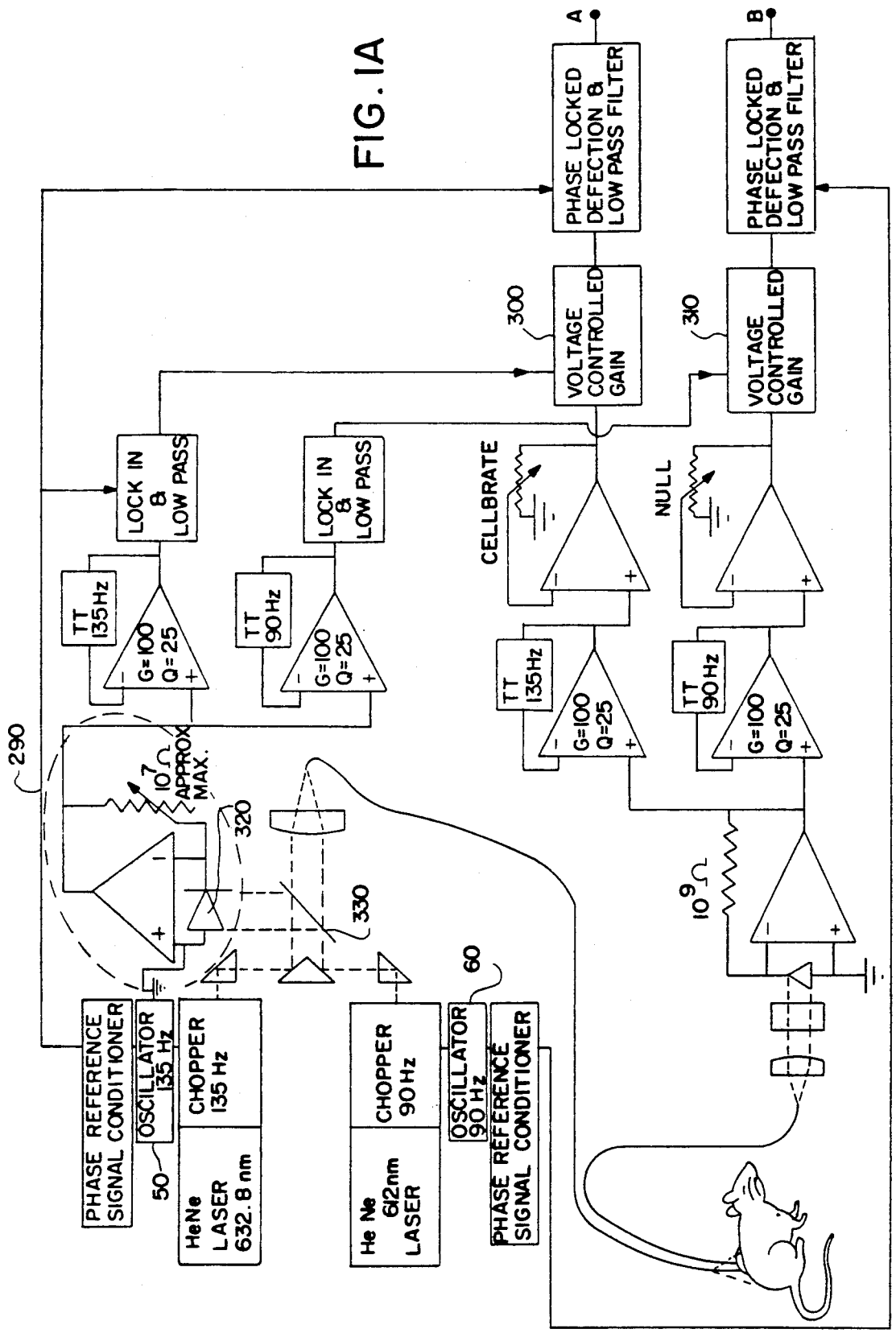
FIG. 1A is a block diagram of an alternative embodiment of the fluorometer of FIG. 1.
Figure 1B:
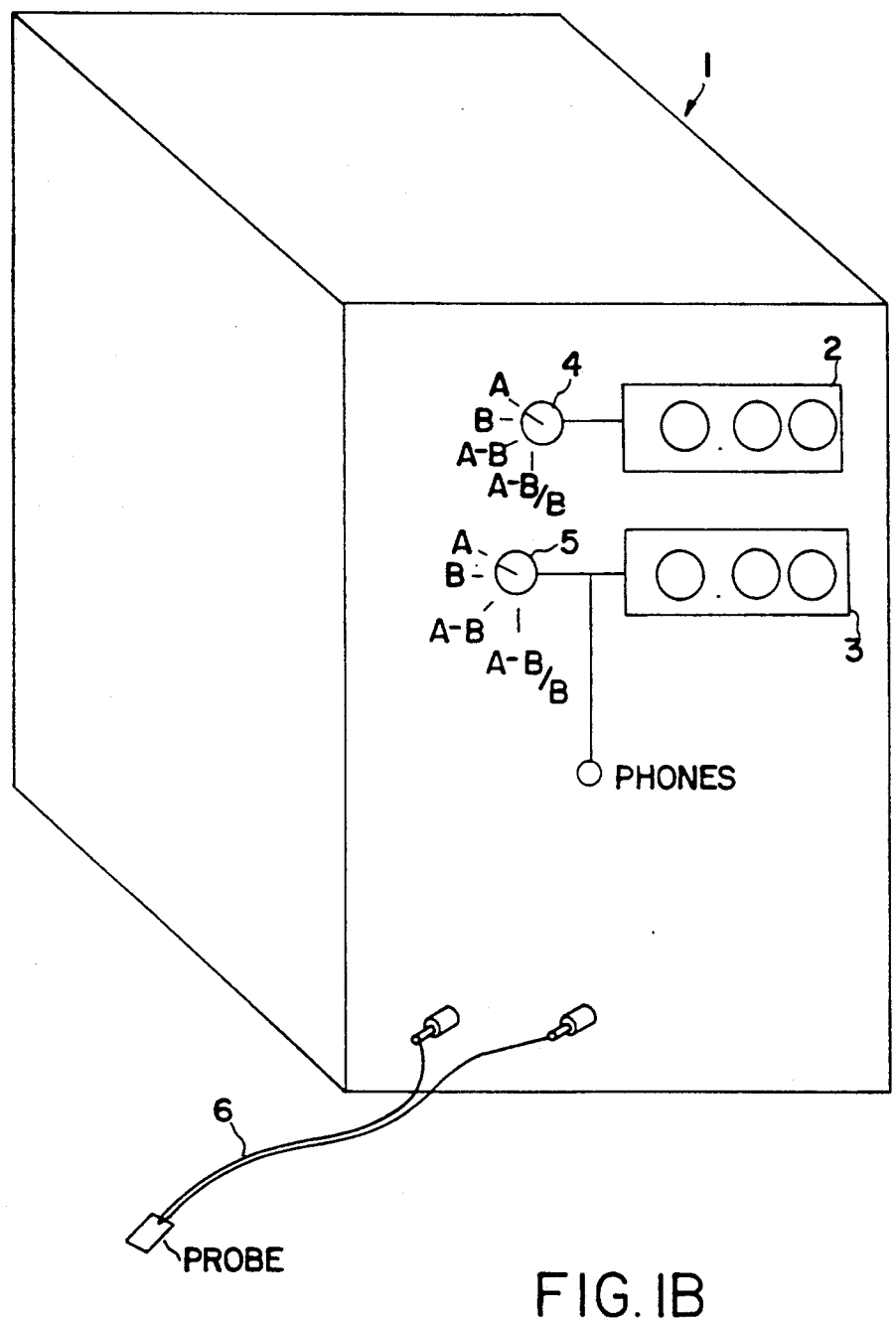
FIG. 1B is a perspective view of a fluorometer of the invention.

FIG. 1B shows the fluorometer 1, which includes digital voltmeter displays 2 and 3 and switches 4 and 5, as well as a probe 6, with functions to be described below.

The choppers 30 and 40 shown in FIG. 1 are driven by oscillators 50 and 60, respectively. Oscillator drives chopper 30 at 135 Hz, and the oscillator 60 drives the chopper 40 at 90 Hz. Each chopper blocks the laser beam exiting from its associated laser at the rate driven by the oscillator in question. Thus, the chopper causes a 135 Hz, 632.8 nm laser beam to reach a prism 70, and likewise a 90 Hz, 612 nm laser beam reaches prism 80. The 612 nm HeNe laser is available from PMS Electrooptics of Boulder, Col., and the 632.8 nm HeNe laser is available from Spectra Physics of Mountain View, Calif. Instead of the 612 nm laser, another laser having a wavelength of approximately 610 nm may be used.

The beams are combined by a prism 90 acting in conjunction with a planoconvex lens 100. The convergent laser beams are fed into an optical fiber 110, and the laser light is conducted thereby to a treatment site, such as treatment site 120 shown in FIG. 1.

The subject or patient, such as rat 130, is first given an injection or otherwise supplied with a sensitizer such as Photofrin II. Such a sensitizer will be preferentially concentrated in the treatment site 120. The Photofrin II will fluoresce due to the excitation of the laser light, in particular due to the laser light at 632.8 nm. As described below relative to FIG. 12, there is a fluorescent peak at an incident wavelength of approximately 630 nm.

As both the tissue background fluorescence (excited by 612 nm and 630 nm) and the Photofrin II fluorescence (excited by 632.8 nm) are detected simultaneously at 690 nm, a means must be provided for separating the two contributions to the 690 nm fluorescence. This is accomplished by the choppers 30 and 40, which cause periodic interruptions in the incident beams and consequently also in the resulting fluorescence at 690 nm wavelength. The apparatus and method for differentiating between the contributions to the fluorescent signal by the 612 and 632.8 nm incident wavelengths are discussed below relative to fluorescence detection.

It is an important feature of the invention that the user is enabled to simultaneously detect the normal tissue background and the abnormal tissue, since this allows the abnormal tissue to be ablated at the same time as detection, with a high degree of accuracy, in an in vivo setting. There are no image registration problems which are inherent in sequential imaging techniques.

The 90 Hz signal (resulting from the 612 nm excitation) represents the tissue background or "B" channel, at 690 nm together with the effects of any stray exciting light which may leak through the 690 nm interference filter 160 shown in FIG. 1. The half-power band pass of this filter is preferably about 10 nm. The 135 Hz signal (resulting from the excitation at 632.8 nm) represents the tissue background fluorescence plus the Photofrin II fluorescence at 690 nm together with stray exciting light.

Because the tissue background excitation efficiency is nearly identical for the 612 nm and 632.8 nm excitation frequencies, the subtraction of the two signals produces (A-B), which accurately represents the Photofrin II signal only for all depths of the tissue, as discussed below. That is, the two exciting wavelengths are close enough together that they behave nearly identically in tissue (have similar scattering and absorption properties) and are nearly identical in their leakage through the 690 nm pass filter used to eliminate almost all of the exciting light from the detector. Thus, it is possible to adjust the amplification of the 690 nm fluorescence produced by 612 nm excitation to cancel signal in normal tissue not containing the Photofrin II (or containing a low level of Photofrin II).

In practice, the magnitude of the background signal is cancelled, i.e. reduced virtually to zero, by adjusting the gain of the "B" channel using normal tissue without the sensitizer present, in the calibration technique described above. More significantly, the random point to point fluctuations can be reduced by a factor of eight in normal tissue with or without a low level of Photofrin II. (The factor of eight was determined by measuring the fluctuations in both the A and B channels by means of voltmeters attached to these channels; the B-channel fluctuations turned out only one-eighth as large as the A-channel fluctuations.)

Fluorescence is picked up through another optical fiber 140, which is preferably held directly against the treatment site 120. Light emanating from the fiber 140 is collimated by a planoconvex lens 150, and is transmitted through an optical band pass filter 160, which may be an interference filter centered on 690 nm, with a filtration band of plus or minus 10 nm. The band pass filtered diode may be a DFA 6900 produced by EG&G Electrooptics and Electronics of Salem, Mass., and the optical fibers may be model number HCR-M400T-12 from Ensign Bickford Optics Company of Avon, Conn.

Figure 1C:
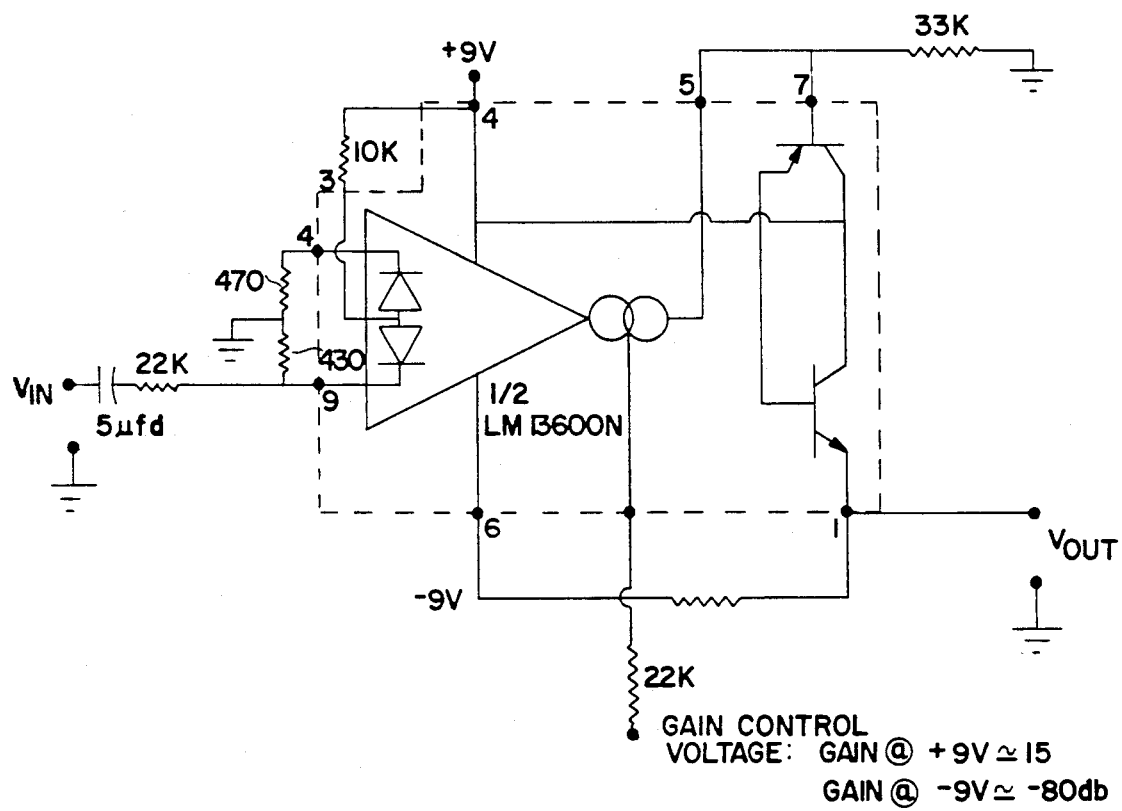
FIG. 1C is a schematic diagram of an amplifier for use with the embodiment of FIG. 1A.
Figure 2:
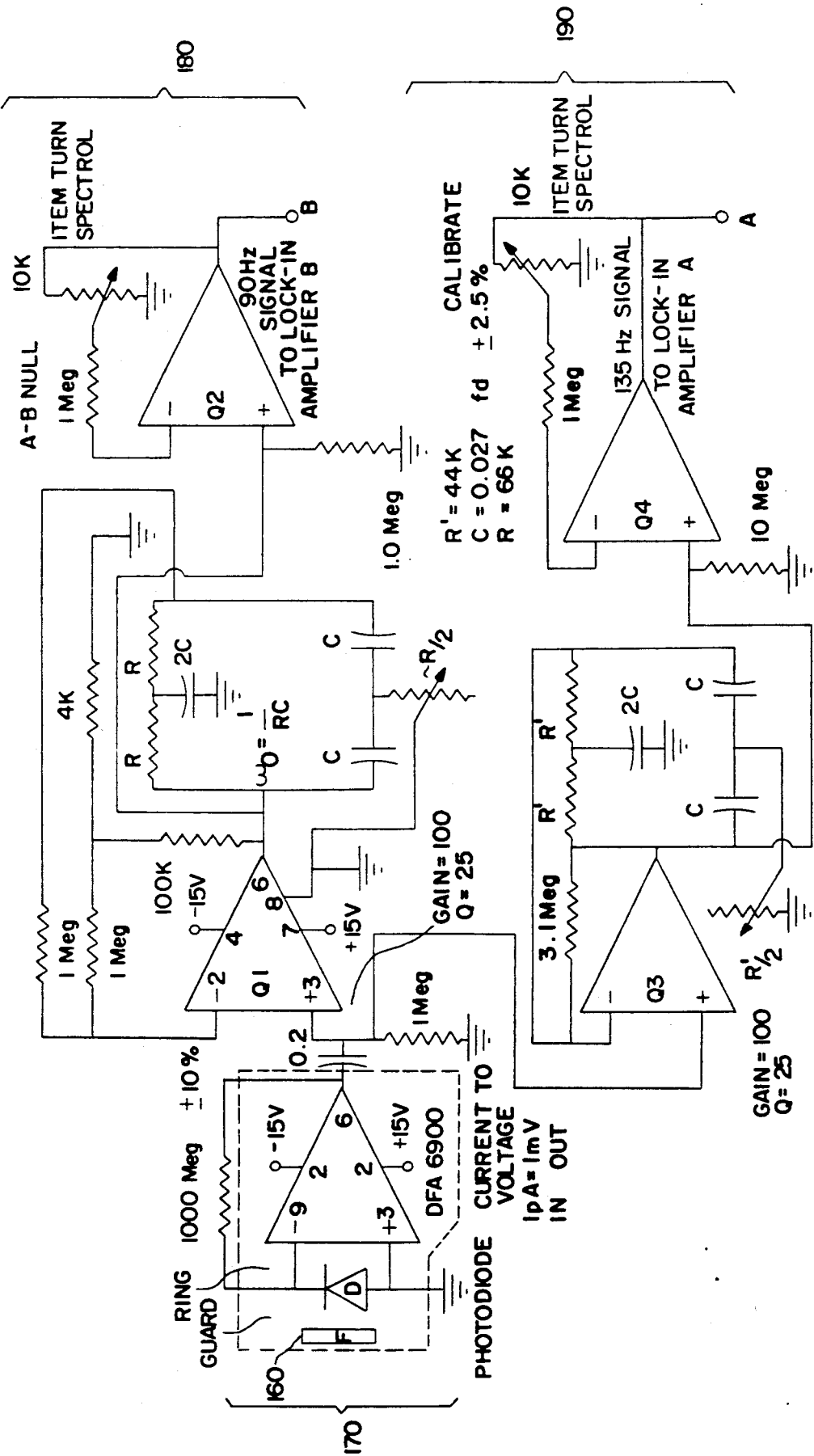
FIG. 2 is a schematic diagram of the fluorescence detector and tuned amplifiers of the fluorometer of FIG. 1.

Once the dual-wavelength optical signal is filtered, it is processed by a fluorescence detector 170, as shown in FIGS. 1 and 2. The fluorescence detector 170 produces a signal relating to the intensity of the input signal, and this is then fed into each of two tuned amplifiers 180 and 190, as shown in FIG. 2. The amplifiers (marked as Q1 and Q3 in FIG. 2) are tuned in a standard fashion by the "parallel T" or "twin T" feedback method. The twin T network has the property of a high impedance at the desired frequency and a low impedance elsewhere. Thus, the amplifiers Q1 and Q3 have a voltage gain of 100 at 90 Hz (Q1) and 135 Hz (Q3), and their gain falls rapidly at other frequencies. The one-half power bandwidth is approximately 5 Hz, and thus the "Q" (representing bandwidth/center frequency) is about 25, which is fairly close to the highest "Q" for which an amplifier can be made unconditionally stable. Circuits with higher "Q" are prone to oscillation.

The gain of the Q1 circuit 180 (and hence the "Q" value) is limited by the feedback provided by the 100K and 4K voltage divider. The gain of the Q3 circuit 190 is achieved in an equivalent manner by using the single 3.1 megohm resistor shown in FIG. 2. The Q3 circuit 190 requires fewer components. Depending upon the open loop gain of Q1 and Q3, the 4K and 3.1 megohm resistors may require some adjustment up or down to achieve a gain of 100. The value of R/2 (shown as a variable resistor at the bottom of circuit 180) is adjusted to approximately 33K, and the value of R'/2 (shown as a variable resistor at the bottom of circuit 190) is adjusted to approximately 22K, and these adjustments are fine-tuned to bring the pin 6 and pin 3 signals of Q1 and Q3 into phase.

The buffer stages Q2 and Q4 are used to prevent loading the amplifiers Q1 and Q3, and to allow the fine-tuning of the gain of each channel.

Channel A is calibrated to give a consistent signal using a standard made by dissolving Kiton Red dye in ethylene glycol. The fluorescence of Kiton Red is extremely stable, and therefore this dye is particularly suitable for laser use. Channel B is adjusted to null the value of A-B when normal tissue or unsensitized tissue is fluoresced. The gain of these stages is typically 3 to 10.

The calibration technique for nulling the signal in channel B due to background fluorescence is as follows. The "A" channel gain is adjusted using the calibration control. A Kiton Red dye fluorescence standard is used for calibration. The Kiton Red (produced by Exciton Inc. of Dayton, Ohio) is dissolved in ethylene glycol (0.0615 g/l). The probe 6 is cleaned using distilled water and lens tissue and held perpendicular to the side of a 1 cm square cuvette containing the fluorescence standard. Care must be taken to avoid letting fingers get in the way, since finger tips are fluorescent. The calibration control is adjusted to give 0.100 volts on the "A" channel digital voltmeter 240.

The null control is then adjusted (A-B) to read −4.200 volts. This will give an approximately zero (A-B) reading on normal human skin without Photofrin II, that is, it has been empirically determined that a reading of −4.200 volts should be used for calibration when the fluorescence standard is Kiton Red, but of course other fluorescence standards might be used for calibration. Moreover, it may be desirable to use another setting for calibration if a very different tissue is used in a particular study or if it is necessary to compensate for a high background level of the sensitizer; although in the latter case, one should probably consider the use of lower doses of sensitizer. The calibration is, of course, carried out before the diagnosis begins.

In order to differentiate between the A and B signals, accomplish this, the signal from the silicon photodiode (produced by the light passing through the filter 160) is fed into two tuned amplifiers and then into two detectors, each of which is phase locked to the appropriate chopper drive signal, as discussed in greater detail below. This technique rejects everything but the fundamental signals of 90 Hz in one channel and 135 Hz in the other channel. Because the two frequencies are at odd half multiples of one another, the phase-locked detection completely rejects any cross interference between channels at the fundamental and at all the harmonics as well. Other frequencies may be used, preferably chosen to exclude common harmonics.

Figure 3:
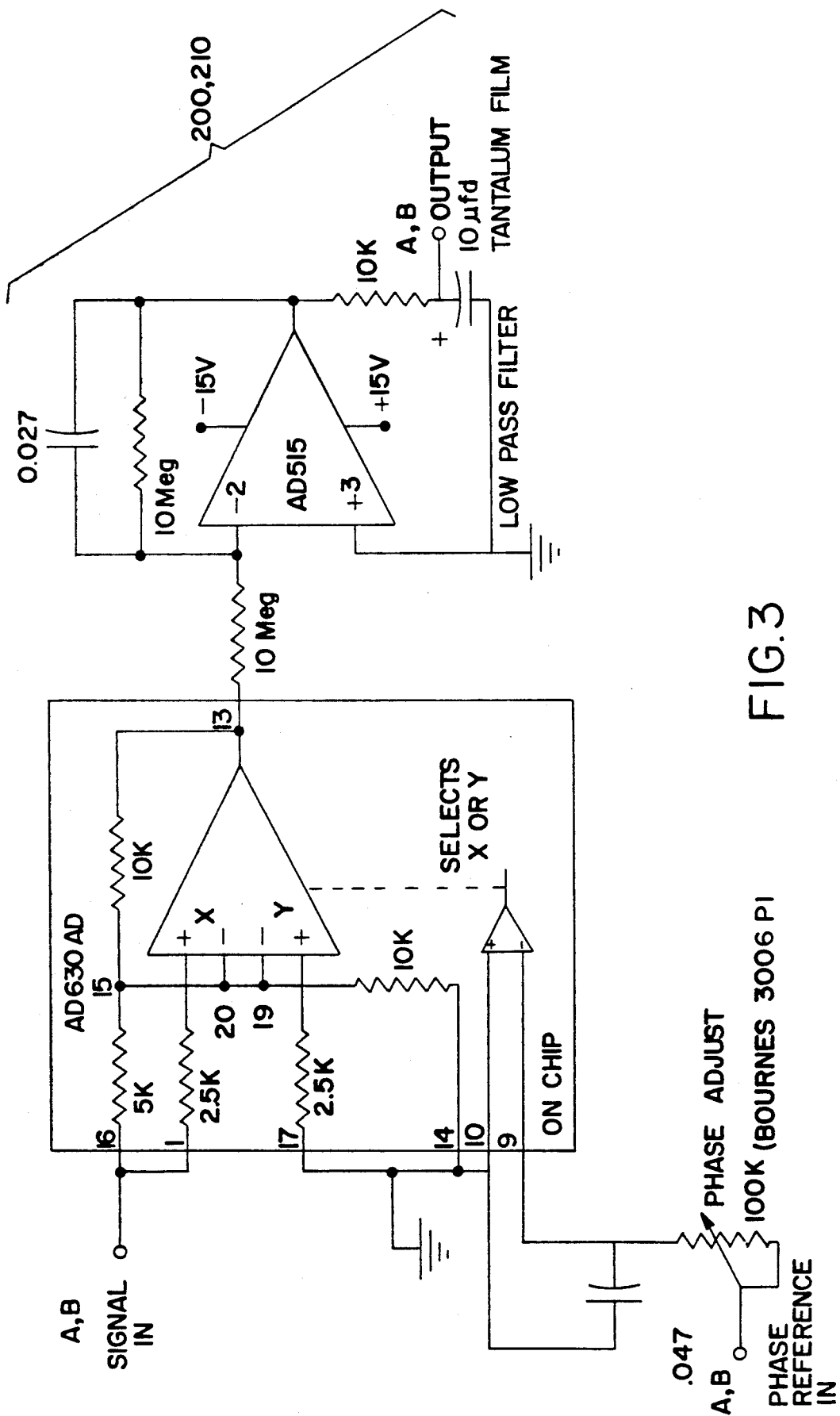
FIG. 3 is a schematic diagram of phase-lock detection and low pass circuitry of the fluorometer of FIG. 1.

The A and B signals, once processed by the circuitry 180 and 190, are fed into the lock-in amplifier circuits 200 and 210, which are identical in structure and are represented jointly in FIG. 3. As shown in FIGS. 1 and 3, a phase reference signal is provided to each of the circuits 200 and 210. Thus, the oscillator 50 has an output which is fed through a signal conditioner 220 and ultimately as a phase reference signal to the amplifier circuit 200. Similarly, the oscillator 60 has an output signal which is fed through the signal conditioner 230, and ultimately as a phase reference signal into the amplifier circuit 210.

In the signal conditioners 220 and 230, the input phase I reference signals from the oscillators 50 and 60, respectively, are square waves. To remove the harmonic content, each square wave is attenuated and then amplified by a stage identical to the tuned stage Q1 or Q3. The conditioned signal should be as close to a pure sign wave as possible for satisfactory phase shifting. In particular, since the degree of phase shift is frequency dependent, it is undesirable to have harmonics in the phase reference signal.

The amplifier circuitry 200 and 210 is similar to that found at Volume I, Section 6, page 65 of *Analog Devices 1984 Databook*. This circuit produces a full-wave detection or rectification and filtration of the signal provided at pin 16 shown in FIG. 3. The detection is in phase with the reference signal applied to pin 9 shown in FIG. 3.

The pin 9 signal selects either an inverting or a noninverting amplification (with a gain of 1) of the pin 16 signal. When the signal on pin 9 changes polarity, the selected amplifier changes. The phase adjustment is used to compensate for phase shift between the mechanical motion of the chopper and the referenced driving voltage.

The AD515 stage shown in FIG. 3 is used to filter the output of the lock-in amplifier. There is a trade-off between noise and band pass, and for noise in the range of 3-5 mv, the 0.1 second time constant produced by the 10 K/10 μfd combination is adequate.

Figure 4:
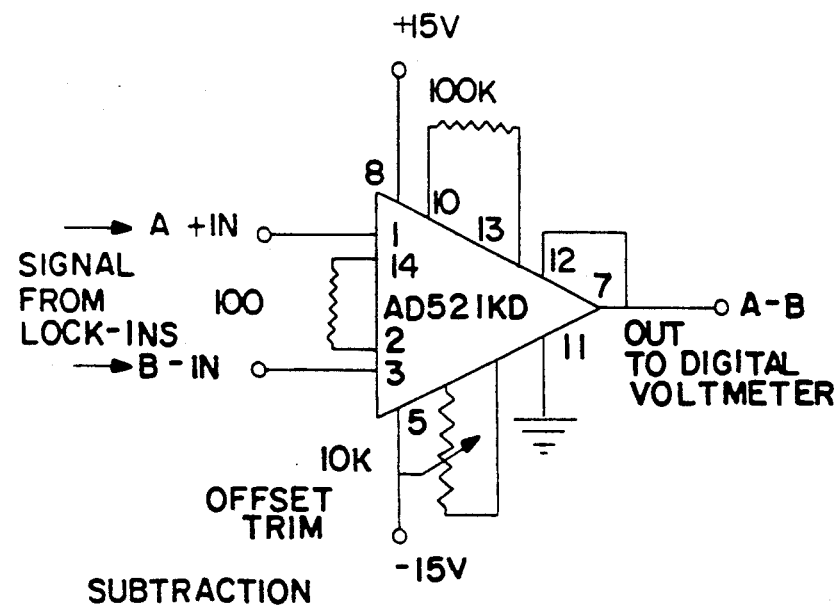
FIG. 4 is a schematic diagram of signal subtraction circuitry of the fluorometer of FIG. 1.

FIG. 4 shows a subtraction circuit utilizing a differential amplifier AD521KD to subtract the filtered output of the two lock-in amplifiers. The signal which results (A-B) is the 690 nm fluorescence produced by the 632.8 nm excitation, minus the 690 nm fluorescence produced by the 612 nm excitation.

Figure 5:
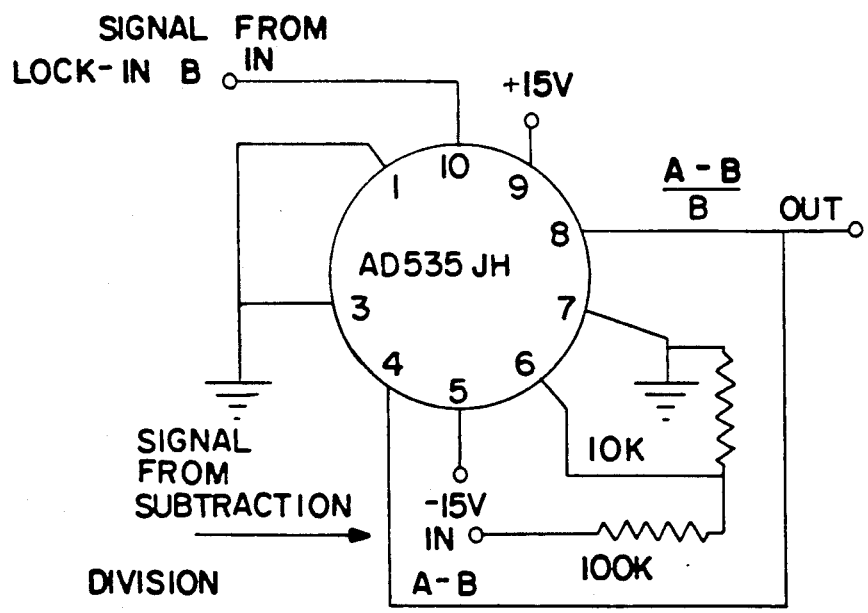
FIG. 5 is a schematic diagram of signal division circuitry of the fluorometer of FIG. 1.

FIG. 5 shows a division circuit which ratios the difference signal (A-B) to the tissue signal (B), which produces a signal (A-B)/B which is independent of the distance the probe 6 may be from the treatment site 120. If the user sets switch 5 (in FIG. 1) such that the (A-B)/B option is chosen, the audio tone will still increase with increase in A (and hence with the presence of abnormal tissue), but the signal will be compensated for accidental variations in the distance from the probe to the diagnostic region, such as tissue 120, by the dividing process. Dividing the difference signal by the background also makes the result independent of the strength of the tissue excitation and of the efficiency of the collection of the fluorescence of the tissue. This quantity, (A-B)/B, is most influenced by changes in the amount of Photofrin II present. It also tends to be independent of spurious changes in the fluorescence signal caused by changes in the optical attenuation properties of the tissue. This is true because the 612 and 632.8 nm wavelengths are close together in a region where the optical properties of tissue do not change radically from point to point in a different fashion for each of these two wavelengths.

Changes in the optical properties or the efficiency of the tissue fluorescence at 690 nm as the probe is moved about would also be perfectly compensated for by (A-B)/B, because such changes would appear as a constant multiplier of both the numerator and denominator of this expression and thus cancel. For instance, if a tumor is buried beneath one to several millimeters of normal tissue, the 690 fluorescence due to the 632.8 nm beam will be attenuated; however, the 690 fluorescence due to the 612 nm incident beam will be attenuated by an identical factor, and thus the attenuation factor will cause the values of A and B to decrease. Since this attenuation factor appears as a multiplier of both A and B, it cancels out in the expression (A-B)/B.

Shown in the lower portion of FIG. 1 are two digital voltmeters 240 and 250, with connections to each of the outputs A, A-B, (A-B)/B and B shown at the upper right of FIG. 1. Each of the commonly-named connector points are connected to one another as shown in FIG. 1. Thus, for example, when voltmeter 250 has its switch 5 connected to connector point B, as shown in FIG. 1, it receives the output B from the amplifier circuit 210.

A voltage-to-frequency converter 260 is connected to the output of the voltmeter 250, and headphones 270 are attached to the converter 260. If the switch 5 of the voltmeter 250 is connected to the (A-B) or (A-B)/B connector points, then as the value of A increase, the frequency supplied to the headphones 260 will also increase. Typically, a clicking noise will be heard in the headphones 270, and a faster clicking, ultimately becoming an apparently continuous and rising pitch, will be heard as the value of A increases. Since the value of A depends upon the 135 Hz signal, an increase in A and hence an increase in the frequency of the signal in the headphones 270, indicates the presence of a greater amount of the sensitizer (such as Photofrin II), which in turn indicates the presence of a tumor. Thus, the operator of the device may utilize the fiber optics to scan a treatment site, and can detect the presence of abnormal tissue simply by listening to the headphones 270.

The voltmeter 240 provides a visual readout analogous to the audio signal of the voltmeter 250, and thus provides a precisely quantified visual signal through the operator. Likewise, the voltmeter 250 may be provided with a visual readout or dial, and thus two visual readouts (which is one for A and one for B) may be provided at the same time as the audio signal over the headphones 270.

Figure 6:
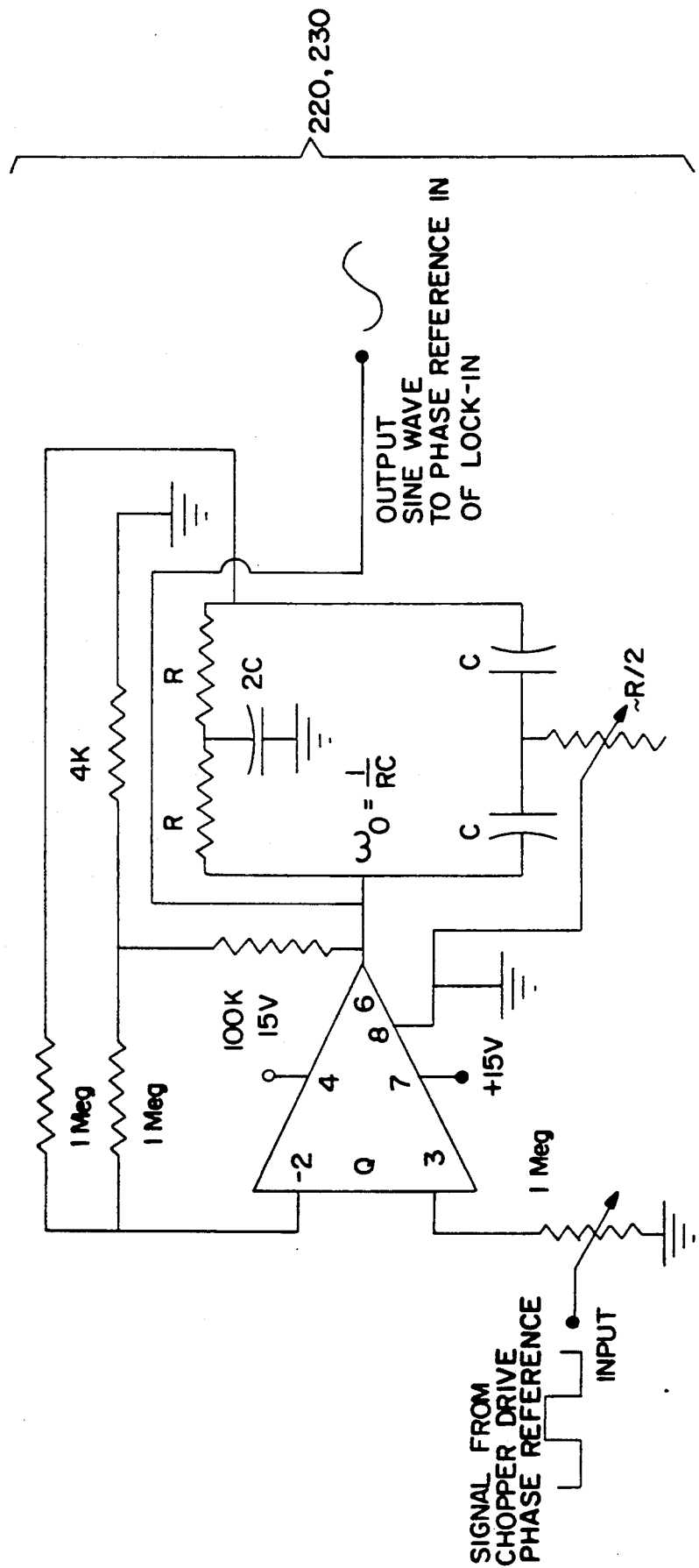
FIG. 6 is a schematic diagram of a phase reference signal conditioner of the fluorometer of FIG. 1.

The signal conditioners 220 and 230 may be of the design shown in FIG. 6, and will be identical except for the value of R, which is chosen to produce the 135 Hz and 90 Hz phase reference sign waves respectively.

Figure 7:
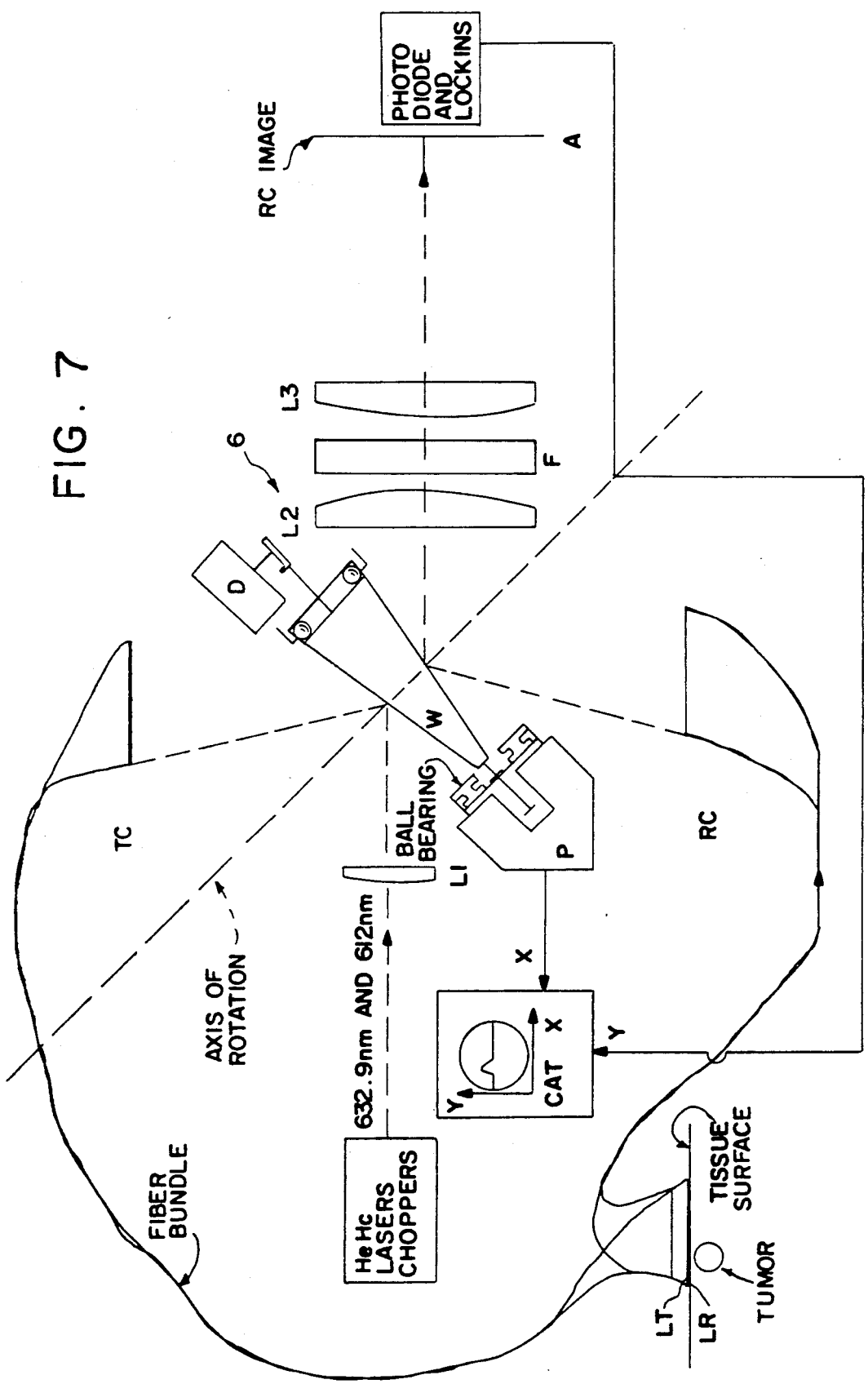
FIG. 7 is a block diagram of an apparatus for generating a linear scan from a rotating detector for use in the invention.

FIG. 7 shows a design for the probe 6 for use in connection with the in vivo fluorometer of the present invention, which will accomplish linear scanning from purely rotary motion. This can be done with an array of fibers. The fibers would be arranged in a straight line at the tissue end of the probe 6 and in a circle at the instrument end of the probe cable. The order of the fibers would need to be preserved (that is, no fibers can be allowed to cross others before the fibers are fastened together side by side at each end). Scanning of the circular end with a laser beam focused to a point is readily done by a round window with a 10° wedge angle (that is, with nonparallel faces). This wedge would deflect the beam as it passed through it and could be rotated about an axis through its center and perpendicular to one of the planes of the wedge. The center of the fiber circle would also pass through the extension of this axis of rotation and the plane of the fiber circle would also be perpendicular to the rotation axis. If the wedge angle, the fiber circle diameter and the lens focal length are appropriately chosen, then the focused spot will sweep around the circle formed by the flat polished ends of the fibers. As this circle of fiber ends is a linear array at the tissue end of the fibers, the effect is to translate to pure rotary motion into a linear scan with essentially no time lag between the end of one scan and the beginning of the next.

This principle could also be used to scan the image of an aperture in front of a filtered detector diode across a second circle of receiver fibers. If the aperture were of the correct size, then all the light from each fiber in turn could be scanned across the detector. Thus, two rows of parallel fibers could be arranged in transmitter and receiver pairs and be sequentially activated to scan a line across the tissue.

Figure 9:
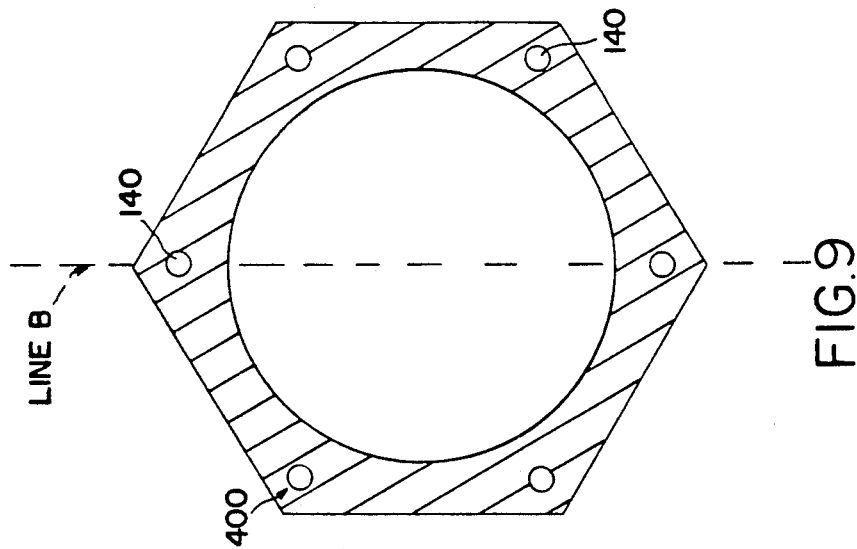
FIG. 9 is an end view taken along line 6—6 of FIG. 5.
Figure 8:
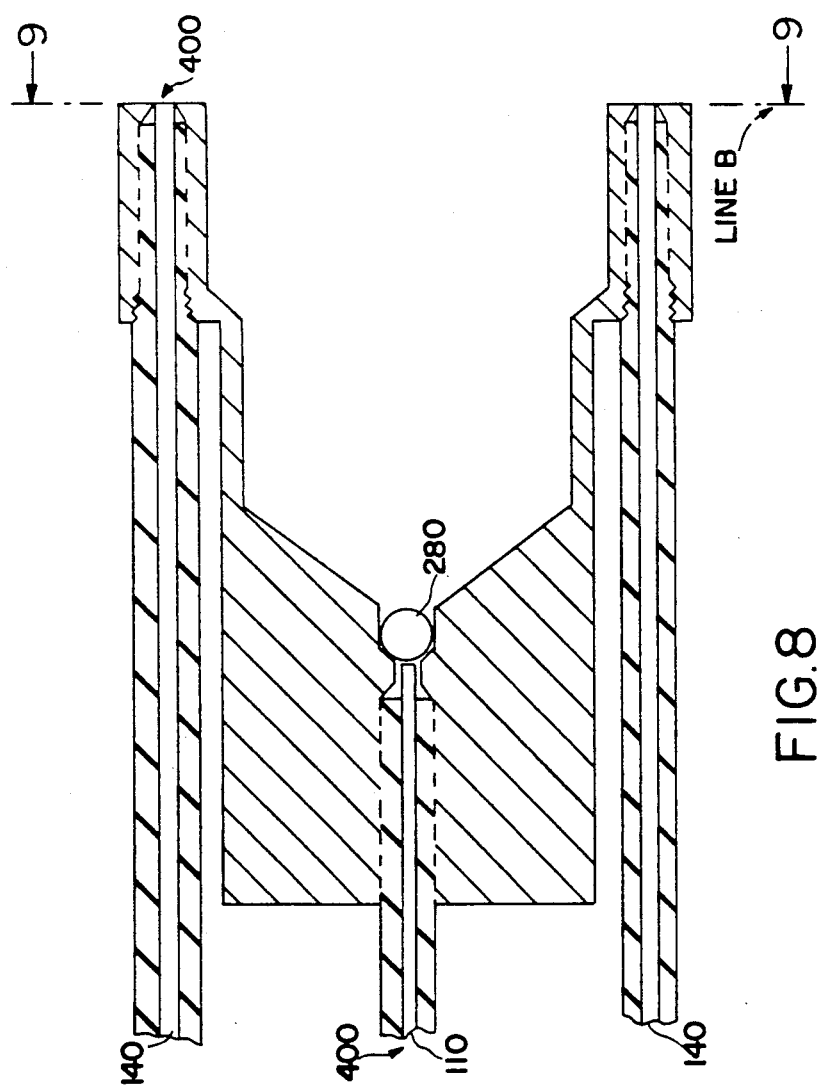
FIG. 8 a cross-sectional view of a surface probe for use in the invention.

FIGS. 8 and 9 show a probe design utilizing a zirconium oxide sphere as a focusing lens for the transmission fiber 110. The receive fiber 140 may by provided in multiple, such that six receive fibers 140 are actually utilized. The utilization of the spherical lens 280 allows for uniform illumination over a circular area, and the equal spacing of the fibers 140 picks up fluorescence from tissue around the periphery of the illuminated circular area.

The surface probe of FIGS. 8 and 9 is especially useful for the examination of large areas (e.g., breast cancer metastatic to the chest wall after mastectomy). Although it is referred to as a "surface" probe, this probe will actually produce an exciting light field with a larger illuminated area wherein the light is more slowly attenuated with depth.

The exciting light is conveyed to the probe by the transmitting fiber. The surface of the end of this fiber is imaged by the 1 mm diameter zirconium oxide sphere onto the surface of the tissue. The advantages of using such a sphere as a lens are several, including that sealing and handling problems during construction are greatly reduced. The sphere is held by a 0.001 inch undersize press fit into the brass body of the probe. This is only possible because of the great mechanical strength of the zirconium oxide sphere, which is available from Precomp Inc. of Great Neck, N.Y. Another advantage is that it provides a highly uniform illumination of the surface.

The six receive fibers which contact the tissue provide a system which compensates for the lower power density of the exciting light, is highly symmetrical (and thus insensitive to probe rotation) and most sensitive to fluorescent targets located beneath the center of the field. The probe is thus capable of accurate localization of deep tumors while at the same time covering an area which is big enough to allow a rapid examination of large surfaces.

FIG. 10 shows another configuration of the probe 6 for use in connection with the present invention, including a receive fiber and a transmission fiber, wherein the receive fiber 140 is 1 cm longer than the transmission fiber 110. In use, the fiber 140 is placed directly against the area to be illuminated, as shown (although not in scale) in FIG. 1 relative to the rat 130, and the transmission fiber 110 illuminates the area adjacent to the point of contact between the fiber 140 and the treatment site. Since fluorescence takes place in a region all around the area illuminated by the fiber 110, such fluorescence will take place immediately beneath the point of contact between the fiber 140 and the treatment site 120.

The transmission fiber 110 is preferably attached to the receive fiber 140 at a distance of approximately 1 cm from the tissue. The fibers are fixed together in parallel fashion by a 1 cm length of heat shrink tubing. The transmission fiber conducts the chopped 612 and 632.8 nm light to the tissue. This results is an illuminated circular field approximately 3 mm in diameter, with a minimally-sized probe. This probe is especially useful for examining lymph nodes of 1-10 mm and for use through the biopsy channels of fiber optic endoscopes.

Figure 11:
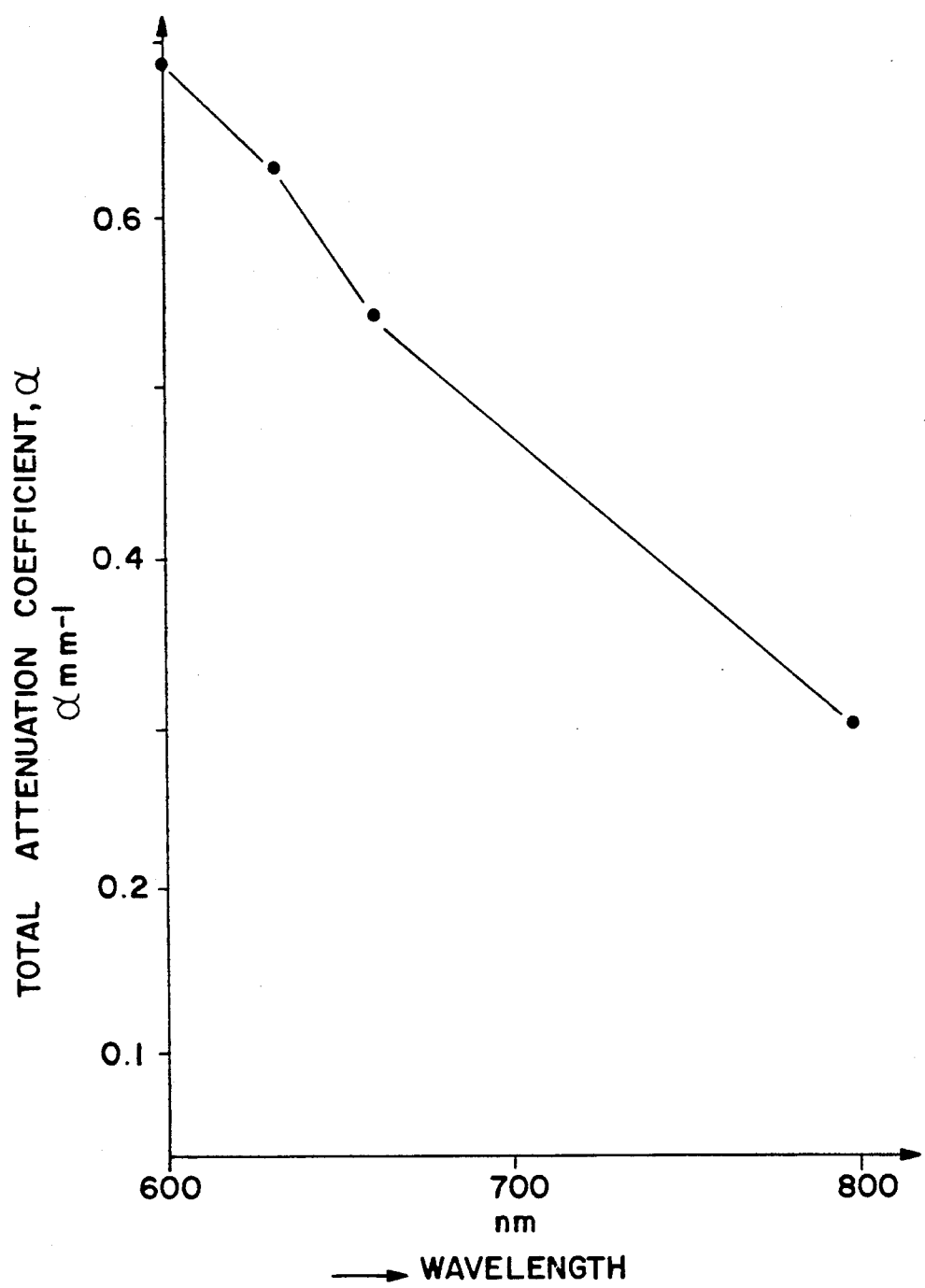
FIG. 11 is a graph showing the variation in attenuation coefficient as a function of wavelength in human tissue.

The method and apparatus of the present invention utilize a relatively long wavelength (632.8 nm) incident light for excitation of the 690 nm fluorescence of the Photofrin II. This is done to allow the maximum depth of noninvasive examination of the tissue. Tissue is more transparent to light in the red region of the spectrum, as reflected in FIG. 11, which shows the attenuation coefficient—that is, the rate at which incident light intensity falls off with increasing distance into the tissue—as a function of wavelength of the incident light. Although the sensitizer absorbs more light in the 400 nm region (see FIG. 12), the tissue absorption makes the 630 nm excitation more efficient for depths greater than about one millimeter.

Figure 12:
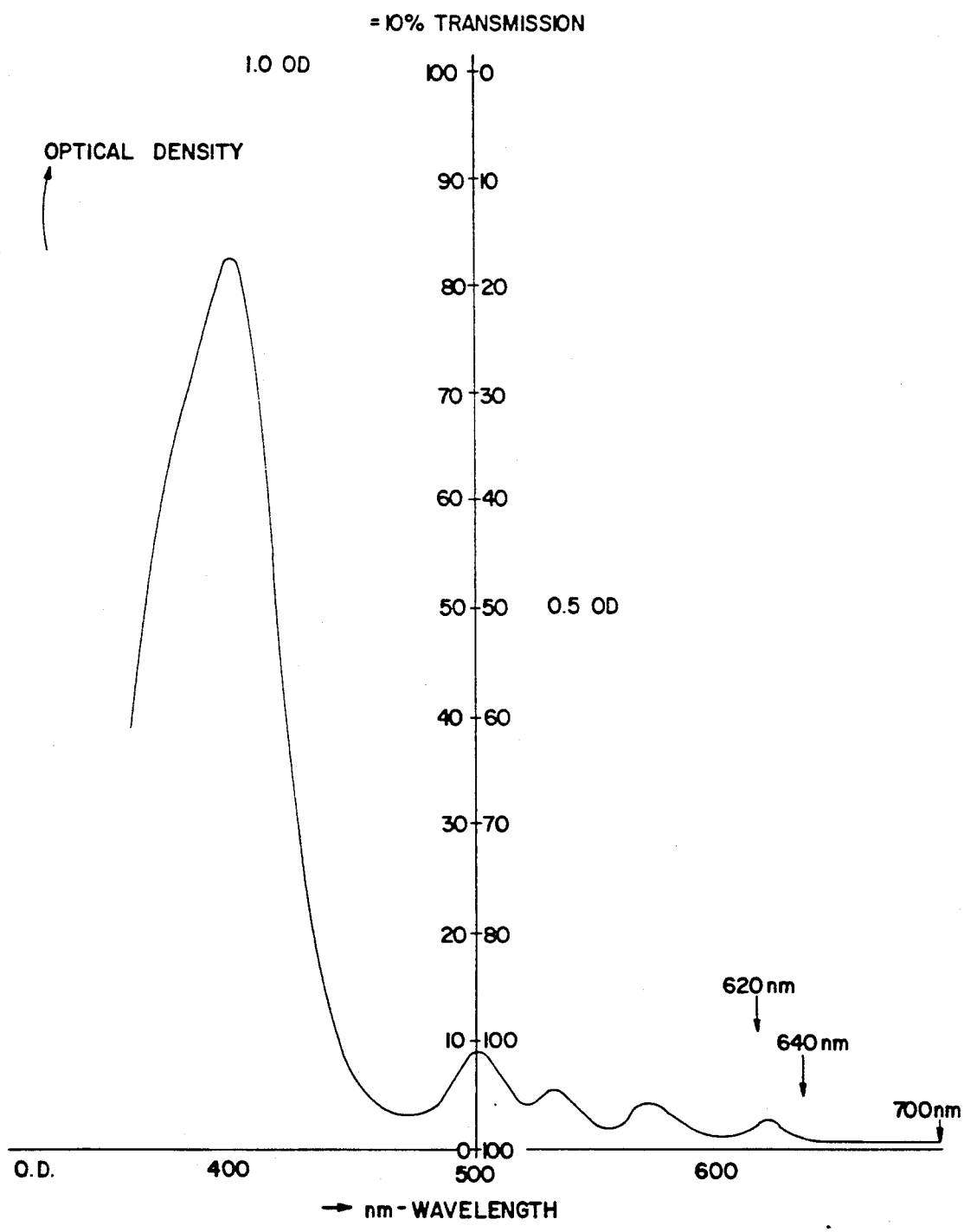
FIG. 12 is a graph showing the absorption spectrum of Photofrin II at 690 nm as a function of wavelength of incident excitation light.

FIG. 12 shows the intensity of fluorescence of Photofrin II as a function of the wavelength of the incident light, i.e. the light that excites the fluorescence. (The wavelength of the detected fluorescent light is on the order of 690 nm.) A very high peak appears at about 400 nm, indicating a high fluorescent response to incident light of this wavelength. The graph of FIG. 12 shows fluorescence peak intensities of decreasing size as the frequency of the incident light goes up, including a peak at about 630 nm. For purposes of penetrating tissue, longer wavelengths are, as described above relative to FIG. 11, more effective. There is thus a trade-off between the intensity of the fluorescent response and the penetrating characteristics of the incident light.

It has been found that the fluorescent response of normal tissue to approximately 630 nm incident light is very nearly the same as the fluorescent response of normal tissue to approximately 612 nm incident light. The present invention utilizes this characteristic by providing incident light of both 612 and 630 nm, in a manner to be described below.

Figure 13:
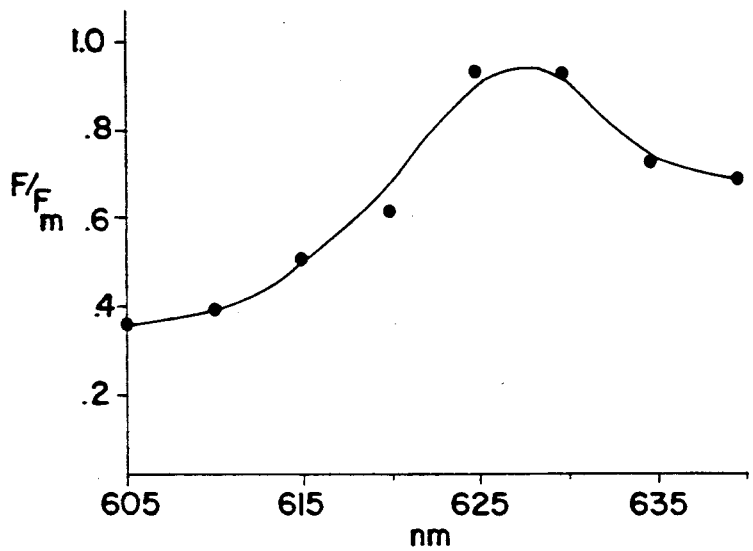
FIG. 13 is a graph showing the in vivo fluorescence spectrum of an amelanomatic melanoma prior to treatment.
Figure 14:
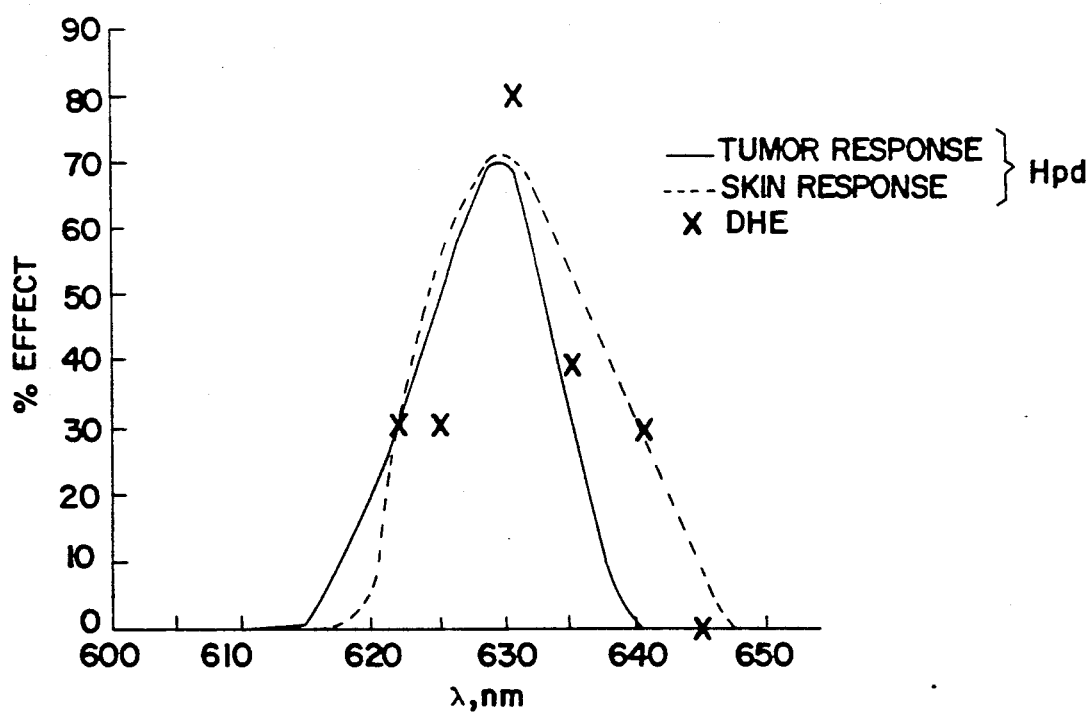
FIG. 14 is a graph showing an in vivo action spectrum showing tumor and skin response to therapy.

The present method is based upon the in vivo absorption band shape of Photofrin II in the 630 nm region and is greatly facilitated by the availability of HeNe lasers to produce the required exciting wavelengths. In FIG. 13, the in vivo biological action spectrum (which corresponds to the in vivo absorption spectrum) is shown for a human patient. In FIG. 14, the in vivo fluorescence excitation spectrum is shown for an amelanotic melanoma in a rat tumor system. Both of these figures demonstrate that the fluorescence intensity peak produced by the approximately 630 nm incident light for Photofrin II in tissue. It will be noted that there is an approximately 5 nm shift between the fluorescence peak in FIG. 12 (which appears at about 625 nm incident wavelength) and those of FIGS. 13 and 14, which appear closer to 630 nm wavelength. This is a result of conducting the tests of FIGS. 13 and 14 in vivo, and the shift in the peak may be a result of binding of the sensitizer to proteins or other substances.

FIG. 13 was produced using an argon ion pumped dye laser as a tunable excitation source for the 690 nm fluorescence of the tissue. The spectrum was collected in a noninvasive fashion using fiber optic probes touching the surface of the patient's skin during PDT treatment. The effects of the tissue background are evident in the failure of the fluorescence to return to baseline away from 630 nm (e.g. at 612 nm). Also apparent is the rise in the baseline as the exciting wavelength increases. This is due to the leakage of the exciting light through the 690 nm pass filter over the detector (a silicon photodiode). The use of the 612 nm light as background cancellation is advantageous because it is as close to the 630 nm peak as possible. That is, the 612 nm wavelength is chosen to be as close as possible to the beginning of the rise of the 630 nm peak on the left side thereof as shown in the graphs of FIGS. 12 and 13, without actually being on the portion with the increasing slope. It has been found that the response of normal tissue to 612 nm excitation is very similar to the response to 630 nm excitation, whereas abnormal tissue treated with Photofrin II responds quite differently to these two wavelengths, as is evident from the 630 nm peak of FIG. 13.

Choice of the 612 nm excitation wavelength for use in conjunction with the 630 nm wavelength therefore results in the best selectivity for the Photofrin II absorption and in the most nearly identical scattering and absorption behavior with depth in the tissue. The two exciting wavelengths will behave in a similar fashion as they penetrate tissue so that the cancellation of background will be accurate at all depths.

In an alternative embodiment, a third wavelength—at, for example, 638 nm, which is adjacent the 630 nm peak on the right side of FIG. 13—could be used to produce an average baseline for background correction. For this purpose a broad spectrum light source such as an arc lamp could be used in conjunction with a diffraction grating three exit slits to provide three different wavelengths for excitation. As an alternative to the diffraction grating, portions of the emission from the arc lamp can be directed through three interference filters to provide three different excitation wavelengths. Other photosensitizers absorbing at even longer wavelengths might also be utilized.

In general, lasers may be preferred as light sources because the beams are spectrally clean and stable with respect to wavelength, and tend to be more reliable and rugged than arc lamp sources. Also, lasers generally provide higher power than arc lamps, which makes it easier to detect the fluorescence signals, and masks noise in the detectors. However, when three or more light sources are used, a single arc lamp may become more practical than several lasers.

Typically, there will be random independent fluctuations in the output of the two HeNe lasers, on the order of approximately 1-2% of total power. Although these power output shifts are small, they can become significant in a subtracted application. In one embodiment, compensation for fluctuation in the HeNe power is accomplished by a voltage-controlled amplifier stage. The output of the HeNe would be sampled using a glass plate at 45° to the beam axis, thus directing a few percent of the power to a photodiode with tuned amplifiers and lock-in detection identical to the fluorescence detection. The signals from these two lock-ins would be used to control the gain of an additional stage of amplification in each of the fluorescence detector channels. Thus, variations in the excitation which are linearly reflected in the fluorescence signal would be canceled by corresponding opposite variations in the amplification of the fluorescence signal and the noise of the system would be reduced and its sensitivity increased.

An apparatus for this purpose is shown in FIG. 1A. which is an alternative configuration to the apparatus of FIG. 1. The circuitry of FIG. 1A includes a tuned amplifier 290 which may be essentially identical to the amplifier 170, except that the resistor in the former is variable and has a range to approximately $10^7$ Ohms. This acts in conjunction with the two conventional voltage-controlled amplifiers 300 and 310 to regulate the amplification of the A and B channel signals, respectively, in response to variations in the output power of the lasers which result, for example, from variations in the line voltage supplied to the lasers.

The amplifiers 300 and 310 may include the LM13600N amplifier produced by National Semiconductor, which is a dual operational transconductance amplifier. One design for the amplifier if FIGS. 300 and 310 is shown in FIG. 1C.

The amplifier 290 includes a photodiode 320 which detects a sample of the beam incident upon a partially reflecting mirror 330. The signals from the amplifier 290 ultimately reach the amplifiers 300 and 310, which compensate for laser output power fluctuations.

STEP-BY-STEP PROCEDURE FOR USE OF THE FLUOROMETER

1. Power up the apparatus—plug in machine and turn it on.
2. Allow a ten-minute warm up.
3. Clean the probe 6 with lens tissue (soft) and distilled water.
4. Calibrate according to the above.
5. Sterilize the probe 6 by soaking it for ten minutes in Cidex (1% gluteraldehyde solution). Then rinse the probe in sterile water.
6. Touch the probe 6 to the tissue of the diagnostic region. Keep finger tips away from the exciting light, since finger tips are fluorescent, even through latex gloves.
7. Notice the reading of (A-B)—or (A-B)/B—and use the rising pitch of the headphone sound as a quick guide to interesting areas of higher fluorescence as the probe is moved over the tissue.
8. Use the large area probe (such as in FIG. 8) to examine large areas of skin or other large surfaces.
9. Examining small (1–10 nm) nodes during surgery is done with the "node probe" (see FIG. 10). This probe is small enough to use through a fiber optic endoscope by passing through the biopsy channel. In this application it may not always be possible to hold the probe perpendicular to the surface and the distance between the tissue and transmitting fiber may be effectively varied. It is for this situation that the (A-B)/B option discussed above was included to compensate for the decreased efficiency that such geometric problems produce in both transmission into the tissue and reception back from the tissue.

10. Areas of high fluorescence may be removed and examined histologically to define the pathology of the tissue. It is helpful to use the fluorometer to guide the excision as the device responds to microscopic amounts of tumor. Similarly, the pathological examination should be exhaustive to avoid missing one or two microscopic nests of tumor cells which can be detected by the fluorometer.

Variations on the foregoing may be made and still utilize the teachings of this invention. For instance, other methods may be utilized for imparting characteristics to the incident light beams so that they may later be differentiated in place of chopping the beams into different frequencies. Other embodiments may be arrived at without departing from the spirit and scope of the invention.

What is claimed is:

1. A method for detecting abnormal tissue in a patient, including the steps of:
    providing the patient with a photosensitizing drug;
    illuminating a diagnostic region simultaneously with first and second wavelengths of incident light;
    detecting fluorescence arising from the incident light from the diagnostic region;
    differentiating between a contribution to the fluorescence due to the first wavelength of light and a contribution to the fluorescence from the second wavelength of the light; and
    providing an output to a user of the method, the output reflecting the differentiation for indicating presence of abnormal tissue at the diagnostic region;
    wherein the illuminating step is carried out by the use of a first laser emitting a 612 nm beam and a second laser emitting a 632.8 nm beam.

2. The method of claim 1, further including the steps of:
    interrupting the 612 nm beam at a first frequency after emission from the first laser and before illumination of the diagnostic region;
    interrupting the 632.8 nm beam at a second frequency after emission from the second laser and before illumination of the diagnostic region; and
    after the illuminating step and before the differentiating step, generating first and second electronic signals having first and second strengths relating to the respective contributions of the first and second beams to the fluorescence from the diagnostic region;
    wherein the differentiating step is carried out by determining the phases of the contributions of the first and second wavelength beams to the fluorescence.

3. A method for detecting abnormal tissue in a patient, including the steps of:
    providing the patient with a photosensitizing drug;
    illuminating a diagnostic region simultaneously with first and second wavelengths of incident light;
    detecting fluorescence arising from the incident light from the diagnostic region;
    differentiating between a contribution to the fluorescence due to the first wavelength of light and a contribution to the fluorescence from the second wavelength of the light; and
    providing an output to a user of the method, the output reflecting the differentiation for indicating presence of abnormal tissue at the diagnostic region;
    wherein the illuminating step is carried out by at least one electrically powered light source, and the differentiating step includes the step of compensating for fluctuations in the power supplied to the light source.

4. A method for detecting abnormal tissue in a patient, including the steps of:
    providing the patient with a photosensitizing drug;
    illuminating a diagnostic region simultaneously with first and second wavelengths of incident light;
    detecting fluorescence arising from the incident light from the diagnostic region;
    differentiating between a contribution to the fluorescence due to the first wavelength of light and a contribution to the fluorescence from the second wavelength of the light; and
    providing an output to a user of the method, the output reflecting the differentiation for indicating presence of abnormal tissue at the diagnostic region;
    wherein the detecting step is accomplished by the use of a probe positioned near the diagnostic region, and further including, after the differentiating step and before the step of providing the output, the step of compensating the output for varying distances between the probe and the diagnostic region.

5. The method of claim 4, wherein:
    the differentiating step includes the steps of generating first and second electronic signals relating, respectively, to the contributions to the fluorescence from the first and second wavelengths, and generating a third electronic signal representing a difference in signal strength between the first and second electronic signals;
    the compensating step includes the step of generating a fourth electronic signal representing a ratio of the third electronic signal to the second electronic signal; and
    the fourth electronic signal is provided as the output to the user.

6. A method for detecting abnormal tissue in a patient, including the steps of:
    providing the patient with a photosensitive drug;
    illuminating a diagnostic region simultaneously with an incident light of a first wave length and an incident light of a second wavelength, said first and second wavelengths being longer than approximately 600 nm, said illuminating step being carried out by an arc lamp having a broad emission spectrum,
    wherein said incident lights of said first and second wavelengths are generated by passing the emission spectrum through a diffraction grating,
    simultaneously with generating light of said first and second wavelengths, generating light of a third wavelength by passing the emission spectrum through the diffraction grating,
    said diffraction grating having at least three exit slits;
    detecting fluorescence arising from the incident lights from the diagnostic region;
    differentiating between a contribution to the fluorescence due to said incident light of the first wavelength, and a contribution to the fluorescence due to said incident light of the second wavelength;
    providing an output to a user of the method, the output reflecting the differentiation for indicating presence of abnormal tissue at the diagnostic region;

simultaneously with the differentiating step, differentiating a contribution to the fluorescence from said light of the third wavelength from the contributions to the fluorescence from the lights of the first and second wavelengths.

7. A method for detecting abnormal tissue in a patient, including the steps of:

providing the patient with a photosensitizing drug;

illuminating a diagnostic region simultaneously with an incident light of a first wavelength and an incident light of a second wavelength, said first and second wavelengths being longer than approximately 600 nm, said illuminating step being carried out by an arc lamp having a broad emission spectrum, wherein said incident lights of said first and second wavelengths are generated by passing a first portion of the emission spectrum through a first interference filter, passing a second portion of the emission spectrum through a second interference filter;

simultaneously with generating said lights of the first and second wavelengths, generating a light of a third wavelength by passing a third portion of the emission spectrum through a third interference filter;

detecting fluorescence arising from said incident lights from the diagnostic region;

differentiating between a contribution to the fluorescence due to said incident light of said first wavelength, a contribution to the fluorescence due to said incident light of said second wavelength;

providing an output to a user of the method, said output reflecting the differentiation for indicating presence of abnormal tissue at the diagnostic region;

simultaneously with the differentiating step, differentiating a contribution to the fluorescence from said light of the third wavelength from the contributions to the fluorescence from said lights of the first and second wavelengths.

* * * * *